(12) United States Patent
Koch et al.

(10) Patent No.: US 9,945,795 B2
(45) Date of Patent: Apr. 17, 2018

(54) CRYSTALS FOR KRYPTON HELIUM-ALPHA LINE EMISSION MICROSCOPY

(71) Applicant: National Security Technologies, LLC, North Las Vegas, NV (US)

(72) Inventors: Jeffrey A. Koch, Livermore, CA (US); Michael J. Haugh, Livermore, CA (US)

(73) Assignee: National Security Technologies, Inc., North Las Vegas, NV (US)

( * ) Notice: Subject to any disclaimer, the term of this patent is extended or adjusted under 35 U.S.C. 154(b) by 214 days.

(21) Appl. No.: 15/073,946

(22) Filed: Mar. 18, 2016

(65) Prior Publication Data

US 2017/0269010 A1 Sep. 21, 2017

(51) Int. Cl.
*G01N 23/20* (2006.01)
*G01N 23/207* (2018.01)

(52) U.S. Cl.
CPC .................................. *G01N 23/207* (2013.01)

(58) Field of Classification Search
CPC ...... G01N 23/00; G01N 23/20; G01N 23/203; G01N 23/207; G01N 23/20008; G01N 2223/1016; G21K 1/06
USPC ...................................................... 378/70, 73
See application file for complete search history.

(56) References Cited

U.S. PATENT DOCUMENTS

| | | | |
|---|---|---|---|
| 3,032,656 A | 5/1962 | Hosemann et al. | |
| 4,426,719 A | 1/1984 | Fraenkel | |
| 4,780,899 A | 10/1988 | Adema et al. | |
| 4,949,367 A | 8/1990 | Huizing et al. | |
| 6,236,710 B1 | 5/2001 | Wittry | |
| 6,259,763 B1 | 7/2001 | Bitter et al. | |
| 6,317,483 B1 | 11/2001 | Chen | |
| 2002/0003662 A1 | 1/2002 | Marcelli et al. | |
| 2012/0256332 A1 | 10/2012 | Maj et al. | |
| 2013/0108022 A1 | 5/2013 | Kugland et al. | |

OTHER PUBLICATIONS

"High-energy x-ray microscopy techniques for laser-fusion plasma research at the Nation Ignition Facility", Jeffrey A. Koch, et al., Applied Optics, vol. 37, No. 10, Apr. 1, 1998, 12 pages.

(Continued)

*Primary Examiner* — Jurie Yun
(74) *Attorney, Agent, or Firm* — Weide & Miller, Ltd.

(57) ABSTRACT

A system for reflecting and recording x-ray radiation from an x-ray emitting event to characterize the event. A crystal is aligned to receive radiation along a first path from an x-ray emitting event. Upon striking the crystal, the x-ray reflects from the crystal along a second path due to a reflection plane of the crystal defined by one of the following Miller indices: (9,7,3) or (11,3,3). Exemplary crystalline material is germanium. The x-rays are reflected to a detector aligned to receive reflected x-rays that are reflected from the crystal along the second path and the detector generates a detector signal in response to x-rays impacting the detector. The detector may include a CCD electronic detector, film plates, or any other detector type. A processor receives and processes the detector signal to generate reflection data representing the x-rays emitted from the x-ray emitting event.

19 Claims, 5 Drawing Sheets

(56) References Cited

OTHER PUBLICATIONS

"4.5- and 8-keV emission and absorption x-ray imaging using spherically bent quartz 203 and 211 crystals (invited)", Review of Scientific Instruments, vol. 74, No. 3, ©2003 American Institute of Physics, Plasma Diagnostics, Mar. 2003, 6 pages.

"Time-resolved ten-channel monochromatic imaging of inertial confinement fusion plasmas", Ingo Uschmann, et al., Applied Optics, vol. 39, No. 31, Nov. 1, 2000.

"Compact imaging Bragg spectrometer for fusion devices", Bertschinger, G., et al., Review of Scientific Instruments, Oct. 2004, vol. 75, No. 10, ISSN: 00346748; DOI: 10.1063/1.1781755, http://scitation.aip.org/content/aip/journal/rsi/75/10/10.1063/1.1781755, http://www.researchgate.net/publication/30047872_Compact_imaging_Bragg_spectrometer_for_fusion_devices/file/3deec528dd41c1a2d2.p.df, (c) 2004 American Institute of Physics, Oct. 2004, 3 pages.

"X-ray instrumentation for protein crystallography with SR", Popov, A.N., et al., E.G., Review of Scientific Instruments, vol. 63, No. 1, pt.11B, 1031, ISSN: 0034-6748; DOI: 10.1063/1.1143190; (c) 1992 American Institute of Physics Jan. 1992, 2 pages.

"Experimental observation of two-dimensional focusing of X-rays in backscattering", Kushnir, V.I., et al., JETP Letters, vol. 48, No. 2, pp. 117-119, ISSN: 0021-3640, Jul. 1988, 3 pages.

"Primary extinction and absorption: a theoretical approach based on the Takagi-Taupin equations. Application to spherical crystals", Chukhovskii, F. N., et al., Acta Crystallographica, Section A (Foundations of Crystallography), vol. 54, No. 2, 191-198, ISSN: 0108-7673, DOI: 10.1107/S0108767397012579, Mar. 1, 1998, 8 pages.

"Bent crystal selection and assembling for the LAUE project", Liccardo, et al., Proceedings of SPIE—The International Society for Optical Engineering, v 8861, 2013, Optics for EUV, X-Ray, and Gamma-Ray Astronomy VI, ISSN: 0277786X, E-ISSN: 1996756X, ISBN-13: 9780819497116; DOI: 10.1117/12.2023617, Oct. 1, 2013, 9 pages.

"Bent crystal analyzer without grooves for inelastic X-ray scattering", Kushnir, et al., Review of Scientific Instruments, vol. 67, No. 9 [+CD-ROM], 5 pp., ISSN: 0034-6748, Sep. 1996, 10 pages.

"Bent crystals by surface grooving method for high-efficiency concentration of hard x-ray photons by a Laue lens", Guidi, et al., Proceedings of SPIE—The International Society for Optical Engineering, vol. 8147, 2011, Optics for EUV, X-Ray, and Gamma-Ray Astronomy V, ISSN: 0277786X, ISBN-13: 9780819487575, DOI: 10.1117/12.895334, Oct. 11, 2011, 3 pages.

"Johansson crystals for x-ray diffractometry and demanding spectroscopy applications", Verman, Boris, et al., Proceedings of SPIE—The International Society for Optical Engineering, vol. 8139, 2011, Advances in X-Ray/EUV Optics and Components VI, ISSN: 0277786X, ISBN-13: 9780819487490, DOI: 10.1117/12.893739, Sep. 28, 2011, 1 page.

"Curved crystals for high-resolution focusing of X and gamma rays through a Laue lens", Guidi, et al., Nuclear Instruments &, Methods in Physics Research, Section B (Beam Interactions with Materials and Atoms), vol. 309, 249-253, ISSN: 0168-583X, DOI: 10.1016/j.nimb.2013.01.070, Aug. 15 2013, 2 pages.

"X-ray crystal devices for measuring compression and stability of laser fusion targets. Final report", Post, B., Sponsor: Department of Energy, Washington, DC.; Report: DOE/DP/10697-T1, 42p, May 1990, 1 page.

"Large aperture point-focusing diffractor for X rays", Wittry, D.B., et al, Applied Physics Letters, vol. 52, No. 17, 1381-1382, ISSN: 0003-6951, DOI: 10.1063/1.99122, Apr. 25, 1988, 2 pages.

"Imaging with Spherically Bent Crystals or Reflectors" M. Bitter, et al., IOP Publishing, Journal of Physics B: Atomic Molecular and Optical Physics, 43 (2010) 144011 (8pp) DOI: 10.1088/0953-4075/43/14/144011, stacks.iop.org/JPhysB/43/144011, Jul. 5, 2010, 9 pages.

CRYSTALS FOR KRYPTON HELIUM-ALPHA LINE EMISSION MICROSCOPY

STATEMENT REGARDING FEDERAL RIGHTS

This invention was made with government support under Contract No. DE-AC52-06NA25946 and was awarded by the U.S. Department of Energy, National Nuclear Security Administration. The government has certain rights in the invention.

FIELD OF THE INVENTION

The invention relates to x-ray imaging and in particular to use of high miller-index crystals for x-ray imaging optics.

RELATED ART

In many applications it is helpful to image emission from energy sources or energy emitted from other events. One such application is for analysis of hot plasmas, where such temperatures can reach the hundreds of thousands of degrees to millions of degrees. Plasma is one of the four fundamental states of matter, the others being solid, liquid, and gas. A plasma has properties unlike those of the other states. A plasma is typically created by heating a gas, or subjecting it to a strong electromagnetic field applied with a laser or microwave generator. This decreases or increases the number of electrons, creating positive or negative charged particles called ions, and is accompanied by the dissociation of molecular bonds, if present.

Such plasmas emit radiation and thus serve as a radiation source and by analyzing this radiation, the plasma may be characterized. Examples of plasmas include, but are not limited, to z-pinch plasma, implosion plasma, or any other type plasma that exists for short periods of time, such as in the nano-second to pico-second range, and are at very hot temperatures. As is understood, plasmas of this nature dissipate very quickly which makes capture of the emitted radiation all the more difficult.

In the event that the plasma is not fully understood, it is desired to better understand the spatial structure of the plasma and the emitted radiation through imaging. During the small window of time when the plasma exists it evolves in shape and the nature of emission. Thus, imaging data representing the plasma or radiation emitted therefrom can be used to characterize the plasma. For example, the distribution and content of emission radiation of the plasma may be of value, as is other data.

Unlike visible light rays, x-rays do not reflect or refract easily. As a result, reflecting x-rays for x-ray imaging presents challenges which are not met by prior art solutions. Prior art approaches for x-ray imaging include use of spherically-bent crystals configured to act as reflective x-ray microscope lenses, much like an aluminized mirror functions as visible light lenses in reflecting telescopes. However, prior art approaches did not meet reflection requirements for many plasma x-ray emissions. The method and apparatus disclosed below overcomes these drawbacks and provides additional benefits.

SUMMARY

To overcome the drawbacks of the prior art several discoveries were made which revealed solutions for prior art drawbacks. Proposed herein are the uses of specific crystals for x-ray imaging. However, crystals only reflect certain x-rays which possess wavelengths that satisfy the Bragg condition. The Bragg condition is an angular condition that must be satisfied for a crystal to reflect a particular wavelength and it depends on the angle of incidence of the x-rays (Bragg angle) and the lattice spacing (2d) of the crystal. For high-quality images to be obtained during x-ray imaging, the Bragg angle needs to be close to 90 degrees (normal incidence) and generally larger than approximately 80 degrees.

Therefore, reflecting x-rays with a particular wavelength is difficult and limited crystals meet image clarity and resolution specification. There are additional challenges in bending this crystal into a nearly spherical surface shape.

To overcome the drawbacks of the prior art and provide additional benefits, a method for imaging from x-rays is disclosed, including generating or receiving x-ray radiation having a wavelength of 0.9518 or 0.9454 angstroms resulting from an event, such as an x-ray emitting plasma. A crystal receives the x-ray radiation. In this method of operation the crystal is germanium, although other materials may be used that meet the requirements. Next, the x-ray radiation reflects from the crystal to a detector. The detector receives the reflected x-ray radiation. The detector is capable of capturing the reflected x-rays.

In one embodiment the event is a plasma with a temperature greater than 1 million degrees Celsius. In one configuration the detector is an image plate. As discussed herein the germanium crystals may be configured with Miller indices of (9,7,3) or (11,3,3). In one embodiment, the reflection angle formed between the x-ray radiation and the reflected x-ray radiation is within 10 degrees of normal. The x-ray radiation may be generated by alpha lines of helium-like krypton. This method may include, prior to reflecting the x-ray radiation, bending the crystal to form an ellipsoidal or spherical shape. The detector may comprise a CCD camera and in response thereto generating a detector signal representing the x-ray radiation.

Also disclosed is a crystal for x-ray reflection of x-ray radiation having a wavelength of 0.9518 or 0.9454 angstroms, such that the crystal comprises a germanium crystal with reflection planes defined by Miller indices of (9,7,3) or (11,3,3). In one embodiment, the reflection plane of the crystal is bent into a spherical or ellipsoidal shape. The crystal may be configured to reflect radiation generated by alpha lines of helium-like krypton. The reflection from the reflection plane is within 10 degrees of normal.

A system for recording x-ray radiation is also disclosed. This system comprises a crystal aligned to receive radiation along a first path from an x-ray emitting event such that the crystal has a reflection plane defined by one of the following Miller indicia: (9,7,3) or (11,3,3). A detector is aligned to receive reflected x-rays that are reflected from the crystal along a second path. The detector generates a detector signal in response to reflected x-rays impacting the detector. A processor is configured to receive and process the detector signal to generate reflection data representing the x-rays emitted from the x-ray emitting event. An output device may provide the image based on the reflected and detected x-rays to display or print the data and subsequent characterizations of the reflected x-rays and/or the event may be established.

In one variation, the reflection data is presented on a display screen in two dimensional graphical format. The x-ray emitting event may be x-rays generated by alpha lines of helium-like krypton in a plasma or other event. The reflection angle between the first path and the second path is within 90 degree plus/minus 10 degrees. In this configuration, the crystal is formed from germanium. The reflection plane may be formed into a spherical or ellipsoidal shape.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION

In various high-energy-density physics (HEDP) experiments, particular x-ray wavelengths of great interest include either component of the helium-like alpha (He-a) line of highly-ionized krypton (Kr). These particular wavelengths are 0.9518 and 0.9454 angstroms. There are no known options for imaging these lines with spherically-bent crystals, and most applications to date have been restricted to wavelengths 2-10 times larger. To overcome the limitations of the prior art, effort was made to find a suitable x-ray crystal with an appropriate lattice spacing just larger than the wavelength.

Disclosed is a novel method and apparatus for producing an efficient x-ray imaging system that images high-temperature plasma in one of the alpha lines of helium-like krypton. In x-ray spectroscopy, K-alpha emission lines result when an electron transitions to the innermost "K" shell (principal quantum number 1) from a 2p orbital of the second or "L" shell. This is just one example of an exemplary emission which may be detected and image using the system described herein. This method and apparatus disclosed herein utilizes a unique match between the wavelengths of these emission lines and two calculated and novel reflection planes revealed by Miller indices in germanium crystals, namely: (9,7,3) or (11,3,3). As discussed above, applications for this technology are in the area of, but not limited to, high-energy-density physics (HEDP), and include microscope imaging of Z-pinch-produced and laser-produced plasmas.

In summary and as discussed below in greater detail, disclosed are two primary options for imaging helium-like alpha (He-a) line of highly-ionized krypton (Kr) at Bragg angles greater than 80 degrees, using germanium (Ge) crystals with large Miller indices. Discovering all non-forbidden reflections of Ge according to the formula 2d=11.3157 angstroms/sqrt of $(h^2+k^2+l^2)$, two Ge Miller indices that are suitable for imaging these lines are discovered, namely: Ge (9,7,3) and Ge (11,3,3). Both of these crystal planes or cuts have the same 2d=0.95978 angstroms, and can be used to image the Kr He-a components with Bragg angles of 83 and 80 degrees, respectively. Materials other than germanium may also be used such as but not limited to quartz. In support of the conclusion, Darwin perfect flat-crystal calculations indicate Ge (9,7,3) and Ge (11,3,3) have ~10 micro-radian rocking curve widths. Additional research has indicated that that bent crystals with these cuts would have even larger rocking curve widths.

Therefore, the disclosed arrangement is a practical way to produce x-ray microscope images with Kr He-a line emission from HEDP plasmas with good efficiency. It is novel to use Ge crystal configurations and cuts for Kr He-a line emission imaging because, among other reasons, such capability is valuable for plasma characterization and other scientific applications.

For example, semiconductor metrology applications and other semiconductor field applications may also benefit from the principles disclosed herein to solve long standing problems in the semiconductor field. For example, manufacturers of bright soft x-ray and EUV sources, such as but not limited to Cymer® and Energetiq® make plasma producing devices. When such devices or any other type x-ray emitting devices utilizes Kr gas (or other x-ray emitting gas) at much higher temperatures, then the innovation described herein may be utilized to focus the resulting emitted x-rays. This might be valuable for lithography and metrology. The company Revera® is another example of a company that may benefit from the disclosed innovation as they offer x-ray metrology solutions. This innovation would provide a source/imaging crystal combination to focus bright Kr line emission down to a small spot on a wafer. Prior art solutions of using electron beam sources are photon-starved and slow. Numerous other real-world application are contemplated.

For better resolution with larger crystal apertures, the crystal surface can be bent to an ellipsoid rather than to a sphere. It is also contemplated that a different Ge crystal may be used, along with other high Miller-index crystals for spherically-bent crystal imaging.

Figure 1:
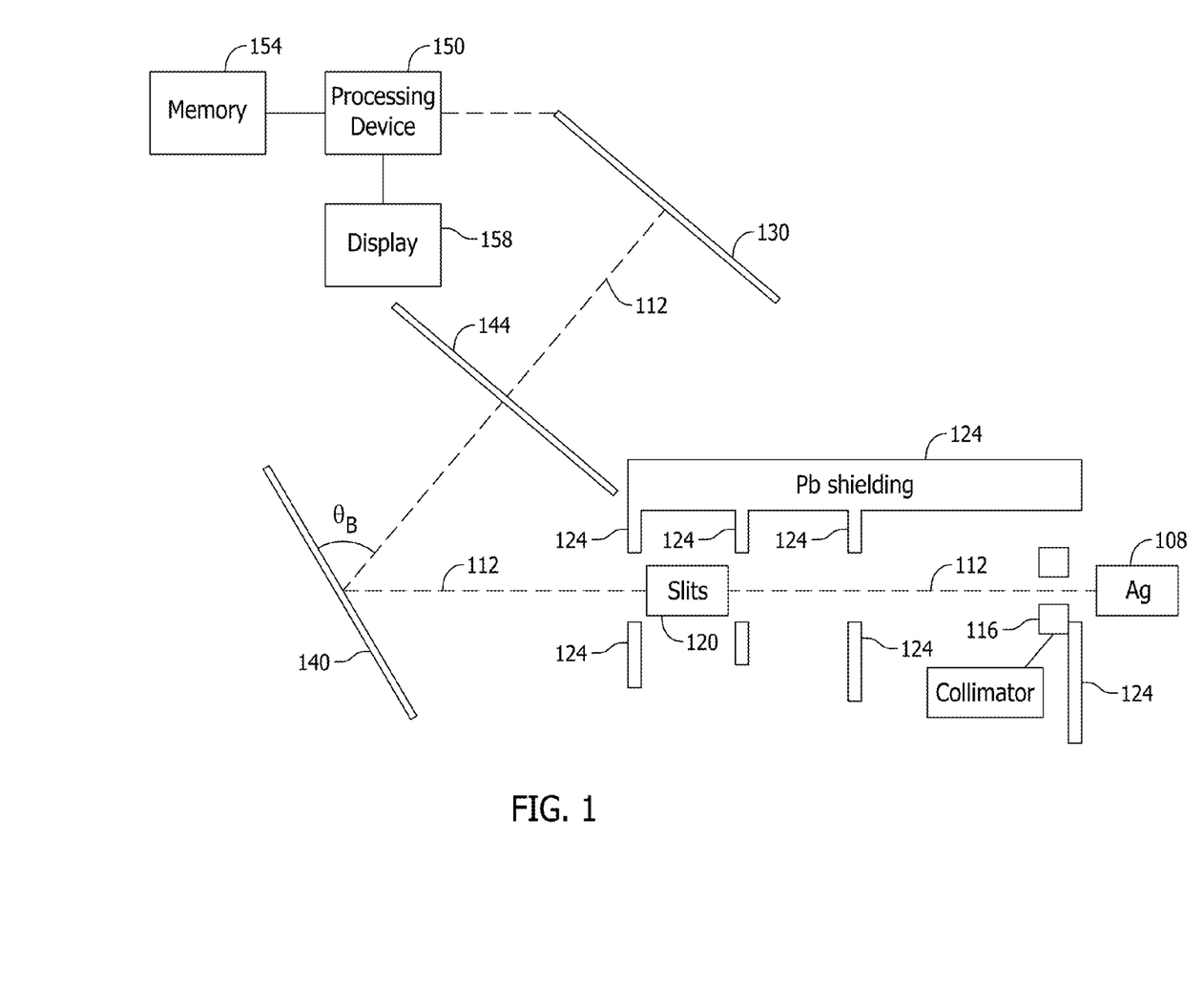
FIG. 1 is a block diagram illustrating an example environment of use of the high-Miller-Index crystals.

FIG. 1 is a block diagram illustrating an example environment of use of the high-Miller-Index crystals. This is but one possible environment of use and as such, one or more elements of FIG. 1 may be substituted with or replaced by other elements, as described below or as understood by one of ordinary skill in the art, without departing from the scope of the invention. As discussed below, the source of the x-rays may vary based on application and the detector may vary based on the application and nature of imaging.

Turning now to FIG. 1, a source 108 is shown which directs energy or any emissions, such as x-rays to a detector 130 after reflection by a crystal 140. Although shown as flat the crystal 140 could be flat, spherical, or ellipsoidal. In this embodiment the source 108 is an Ag based x-ray source. For example, Ru or Ag He-α imaging of burning inertial confinement fusion cores may serve as the source, or any type plasma that emit x-ray radiation, subject to the Bragg condition being met for the crystal 140 and x-ray wavelength relationship. The source 108 may comprise any type event that emits x-ray radiation, such as a plasma.

An x-ray path 112 is provided from the source 108. The x-ray path passes through an optional collimator 116. The collimator 116 is a known device and is configured to narrow a beam of particles or waves to cause the x-rays to become more aligned in a specific direction or to cause the spatial cross-section of the x-rays to become smaller. After the x-ray path 112 passes through the collimator 116, the path enters or passes through one or more slits 120 configured to control or establish the divergence of the x-ray beam. Slits 120 are generally known by one of ordinary skill in the art and as such are not described in detail herein. Slits 120 or an equivalent may be purchased from Newport® Inc. located in Irvine, Calif.

Between the source 108 and a detector 130 is one or more shields 124 which prevent or inhibit errant x-rays from reaching the crystal 140 and the detector 130. The arrangement of shields 124 shown in FIG. 1 is exemplary and other shielding layouts are contemplated. The shields may comprise lead or any other material(s) capable of absorbing x-ray energy.

After the slits 120, the x-ray path 112 is directed to the crystal 140. Any type crystal material may be utilized that meets the Bragg condition and the ability of the crystal and the crystal alignment to reflect the x-rays of interest. A single crystal plane or multiple crystal planes may be established. In this embodiment the crystal 140 comprises a germanium crystal having a high Miller index, such as Ge (9,7,3), or Ge (11,3,3). The alignment of the crystal is such that the angle $\theta_B$ is generally between 80 degrees and 90 degrees.

After reflection or re-direction of the x-rays of interest from the crystal 140 the x-rays are presented to a filter 144. An x-ray filter is a device to block or filter out some or all wavelengths or energy bands in the x-ray spectrum. The filter 144 may be placed before or after the crystal 140. The filter 144 may be configured to allow only a single X-ray wavelength to penetrate to the crystal or from the crystal. The filter 144 may also be selected based on scattering and the diffraction distance. In this configuration the filter is a Cu (copper) based filter but in other embodiments or configurations other filters types or materials may be adopted for use.

A detector 130 receives the x-rays that pass through the filter 114 along the filter path 112. The detector 130 may comprise any type detector capable of capturing and recording x-ray emissions. In one configuration the detector 130 is capable of x-ray imaging. The detector 130 may comprise but is not limited to an image plate, a CCD camera, film, photographic film, a gated micro channel plate detector, which is similar to CCD but with rapid action gates, or any other type detector capable detecting x-rays of interest.

In certain embodiments a processing device 150, such as a computer or specialized electronics, connects to the detector to receive an electrical signal indicating or representing x-ray data. The processing device 150 may process the data to form an image, which may be printed or displayed on a display or screen 158. A memory 154 is provided and stores machine readable code in a non-transitory state that is executable by the processing device to perform the analysis of the data from the detector 130. The memory 154 may also store the data.

Figure 2:
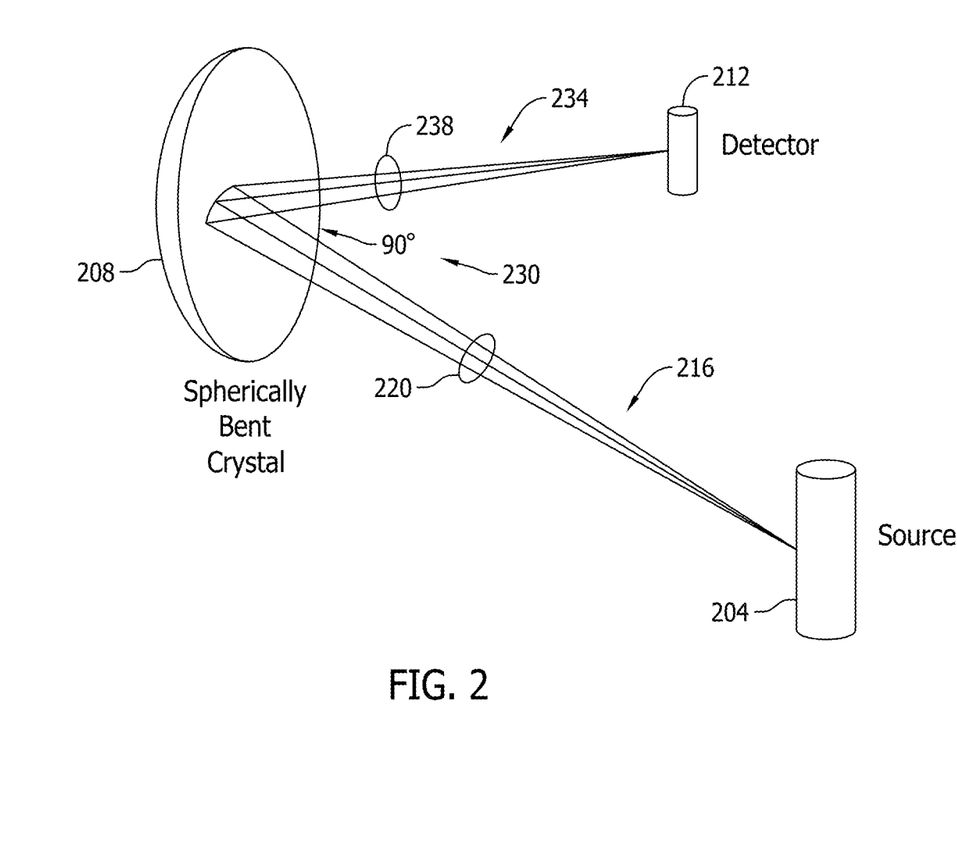
FIG. 2 is a generalized diagram of a curved or spherical crystal reflecting x-rays toward a detector from an x-ray emitting event.

FIG. 2 is a generalized diagram of a curved or spherical crystal reflecting x-rays toward a detector from an x-ray emitting event. This figure shows a perspective view of the reflection arrangement between the source 204, such as a hot plasma, the crystal 208, and a detector 212. The source 204 emits x-ray energy, or other type energy which is directed to the crystal 208. In this embodiment the crystal 208 is spherically bent, such as a concave reflect surface, but in other embodiments the crystal may be planar, curved in only one dimension, or have multiple planar surfaces with multiple angles. For example, but not limited to, the surface may be spherical or ellipsoidal, or any other shape.

The emitted x-rays 216 from the source travel to the crystal and may diverge into multiple rays or paths 220. Upon reflection from the crystal, the reflected rays 234 are directed to a detector 212. The reflection angle 230 between the emitted x-ray path and the reflected x-ray path is between 80 degrees and 90 degrees. The reflected x-rays may be considered as multiple rays or paths 234 near the crystal 208 and converge at the detector 212.

Figure 3:
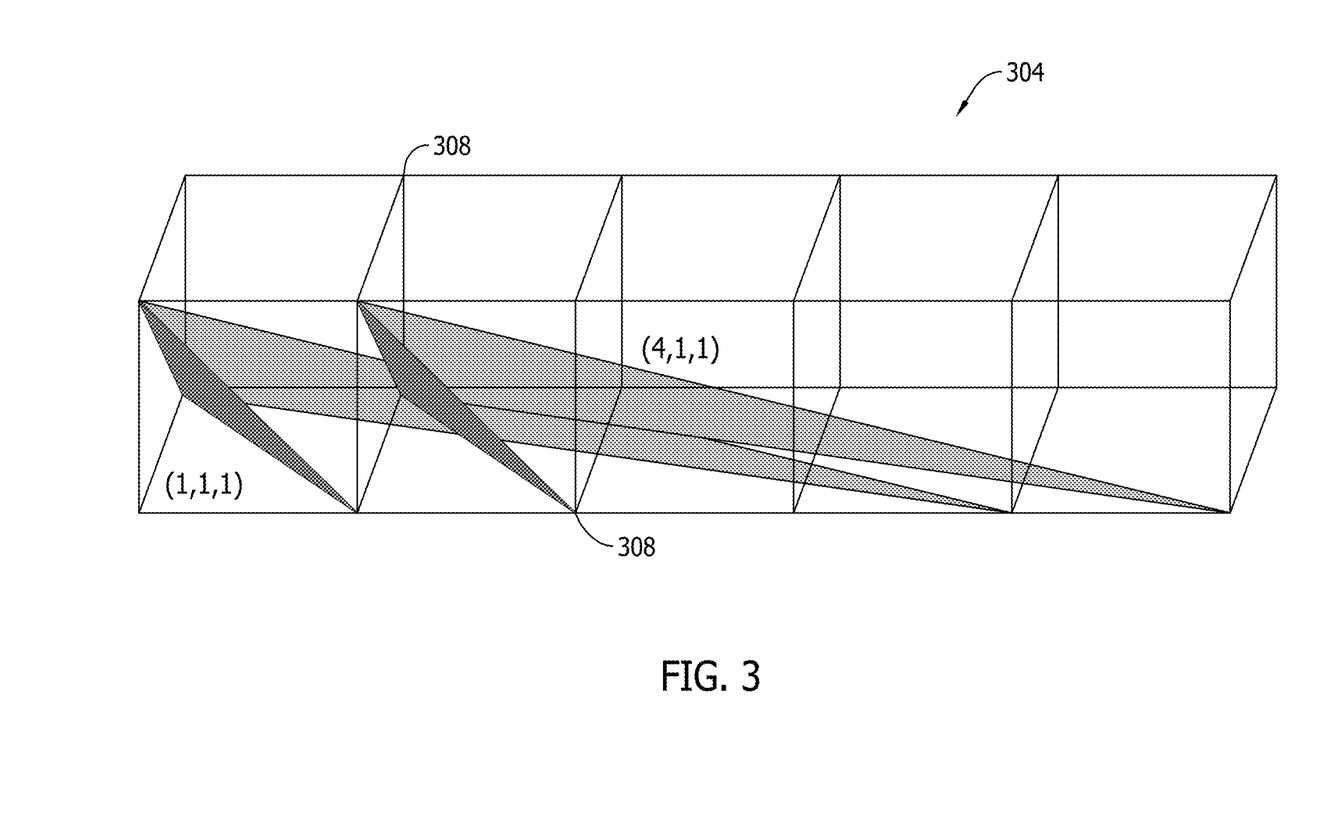
FIG. 3 illustrates an exemplary crystal lattice.

FIG. 3 illustrates an exemplary crystal lattice. This is an exemplary structure provided only for the purposes of discussion and explanation and does not accurately represent the crystal, dimensions, proportions, or molecular structure used with the x-ray lines, wavelengths and other system parameters described herein. One of ordinary skill in the art, in connection with FIG. 3, will understand the crystal structures as defined by Miller indices. Miller indices form a notation system in crystallography for planes in crystal lattices. In particular, a family of lattice planes is determined by three integers h, k, and l, which are defined as the Miller indices. These integer values are commonly written as (h,k,l). As shown in FIG. 3, a crystal 304 includes lattice points 308 that define the shape of the molecular crystal structure. The figures shows index points (1, 1, 1) which define a unique plane and (4,1,1) which defined a different unique plane. Planes of interest for the disclosed system and method include Ge (9,7,3), and Ge (11,3,3).

By selecting and configuring crystals with the Miller indices defined herein or other Miller indices, the crystal is configured to reflect the x-ray wavelengths of interest. In prior art solutions, the standard approach was to utilize a high order n of a conventional crystal cut with low Miller indices (h,k,l). However, this yields limited energies which satisfy the Bragg equation $n\lambda \approx 2d$. The proposed and unexpected solution disclosed herein is to utilize high Miller-index crystals which naturally yield small 2d values for diamond structure based on the following equation, where $d_{hkl}$ defines the lattice spacing, the values h, k, and l are the Miller index values and $a_0$ is the lattice constant.

$$2d_{hkl} = \frac{2a_0}{\sqrt{h^2 + k^2 + l^2}}$$

This approach results in a greater number of options for near-normal-incidence ($n\lambda \approx 2d$) crystal imaging at high x-ray energies and many closely spaced choices of (h,k,l). A further benefit is that no or only minor low-order contamination from lower-energy x-rays is present because n=1. However, one drawback of using of high Miller-index crystal planes is that such planes are typically novel and unexplored, and thus have unverified reflectivity.

Crystals formed from germanium having Miller indices of Ge (9,7,3) and Ge (11,3,3) may be custom made including by custom order from companies specializing of creation or grinding of unique crystal with unique crystal planes. Once such vendors is Inrad Optics® located in Northvale, N.J.

As a benefit to the method and apparatus described herein, use of spherically bent crystals for x-ray imaging is very efficient, with line sources at Bragg angles close (such as within approximately ~6 degrees) to normal incidence, enabling high-quality photon-rich data collection over mm fields of view. The resulting images may be highly monochromatic (defined by $E/\Delta E < 10^{-4}$), but have high spatial resolution (such as >2 µm). The typical applications for this method of operation are typically at keV x-ray energies, up to 8 keV (Cu K-$\alpha$), but it is contemplated that other energy levels.

Higher x-ray energies (10-50+ keV) are of great interest for numerous research installation and applications, but spherical crystal imaging is challenging at these energies due to a lack of reflecting crystals. For example, small λn values may be used such that the λ values are much less than typical inter-atomic spacing (typically by several angstroms). In addition, high x-ray energy imaging is also challenging because of low reflectivity of the x-ray on the crystal surface, necessitating large apertures, high crystal quality, and Bragg angles very close to 90° to limit geometrical aberrations. The method and apparatus overcomes these drawbacks.

Figure 4:
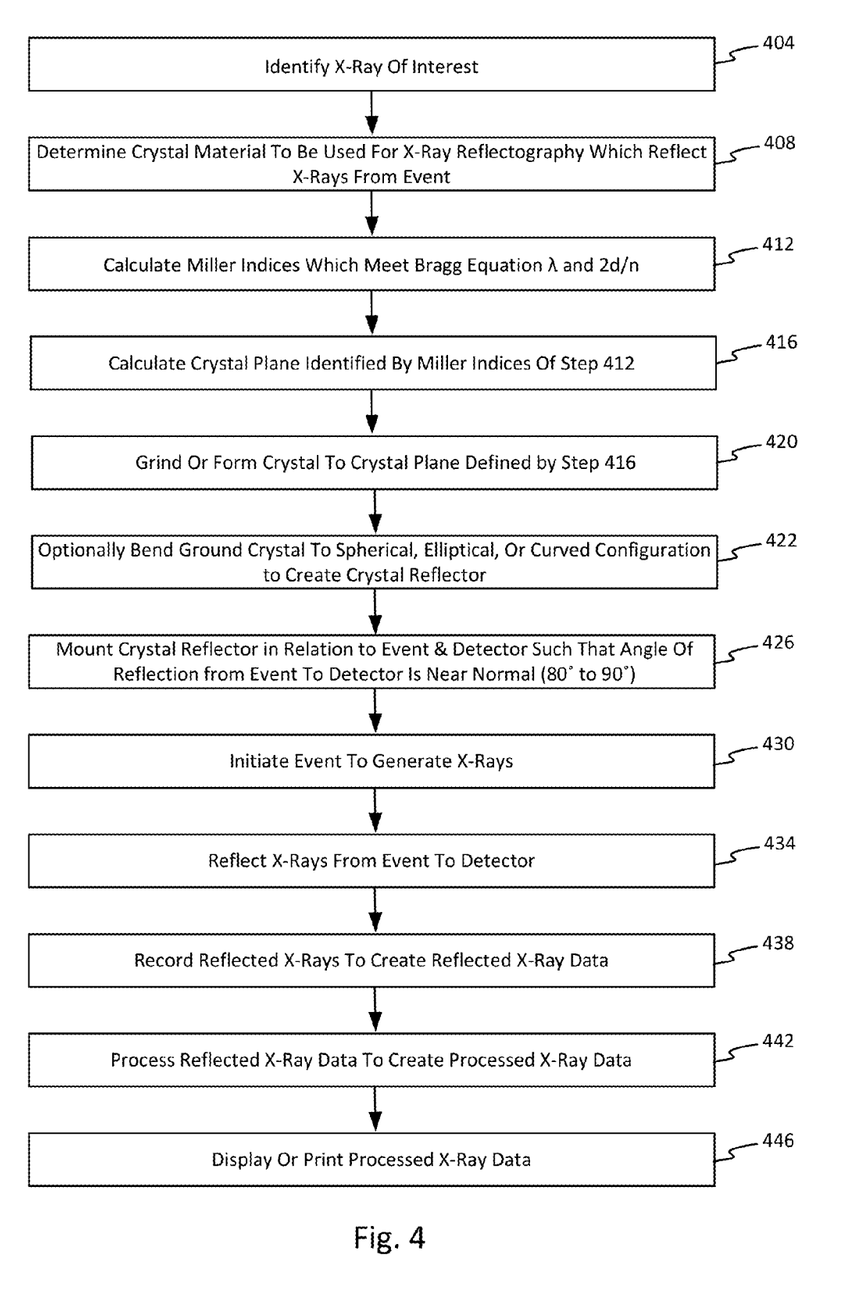
FIG. 4 is an operational flow diagram of an example method of operation.

To realize these benefits, FIG. 4 presents an operational flow diagram of an example method of operation. This is but one possible method of operation and one of ordinary skill in the art may arrive at other embodiments and configurations.

Working from this foundation and turning to FIG. 4, at a step 404 the x-rays of interest are identified. This may be based on the event being studied, x-ray wavelength, or other factor of the detection process. Based on the x-ray of interest, the process determines a crystal material to be used for x-ray reflectography such that the identify crystal will reflect the x-rays of interest. This occurs at a step 408. At a step 412 the process calculates the Miller indices which meet the Bragg equation:

$$2d_{hkl} = \frac{2a_0}{\sqrt{h^2 + k^2 + l^2}}$$

Then, at a step 416, based on the identified Miller indices at step 412, one or more crystal planes may be calculate or determined as being ideal or preferred for x-ray reflection. In one embodiment the Miller indices comprise Ge (9,7,3) and Ge (11,3,3).

Using the identified Miller indices, at a step 420, the crystal is ground or formed to the crystal plane defined by step 416. The grinding or forming of the crystal to a given set of Miller indices is known by one of ordinary skill in the art and typically performed by a company specializing in such tasks once the company is provided with the specifications, material, and Miller indices. As part of or after crystal grinding/forming, the resulting crystal may be optionally bent or ground into a spherical, elliptical, or curved configuration to create a crystal reflector. This occurs at optional step 422. Crystal bending is a complex process but may be performed by the company grinding the crystal or by a third party company, such as Inrad Optics® located in Northvale, N.J.

Once the crystal reflector placement is complete, the operation advances to step 426. At step 426, the crystal reflector is mounted, in relation to event and the detector, such that an angle of reflection from event x-rays (along a first path) to the crystal and then (along a second path after reflection) to the detector is near normal (80° to 90°). FIG. 2 illustrates this angular relationship. Next, at step 430 the event is initiated or occurs to generate the x-rays of interest. Any type event may be used to generate the x-rays, but one typical source is a plasma. At a step 434, the x-rays emitted from the event are reflected to the detector. Because the crystal meets the Bragg condition, the x-rays are adequately reflected to the detector.

At the detector, during a step 438, the detector records, detects, or captures the reflected x-rays or x-ray energy which in turn establishes reflected x-ray data. The data may represent intensity of the x-rays, the number of detections, image data, location of the x-rays strikes on the detector, presences of certain x-ray types, or any other type of detector data. At a step 442 the reflected x-ray data generated by the detector is processed to create processed x-ray data. The processing may be performed by a computer, processor, controller or other data processing element. As discussed above, the processor may operate in connection with a memory, a user interface, and a display screen. Thereafter, at a step 446, the processed data is displayed on a screen to a user or printed for analysis. In addition, one or more types of analysis may be performed on the data.

It is contemplated that the data processing and interface with the detector may be performed using the exemplary computing elements described below and illustrated in FIG. 5. The computing elements may be established as part of a network or as a stand-alone system.

Figure 5:
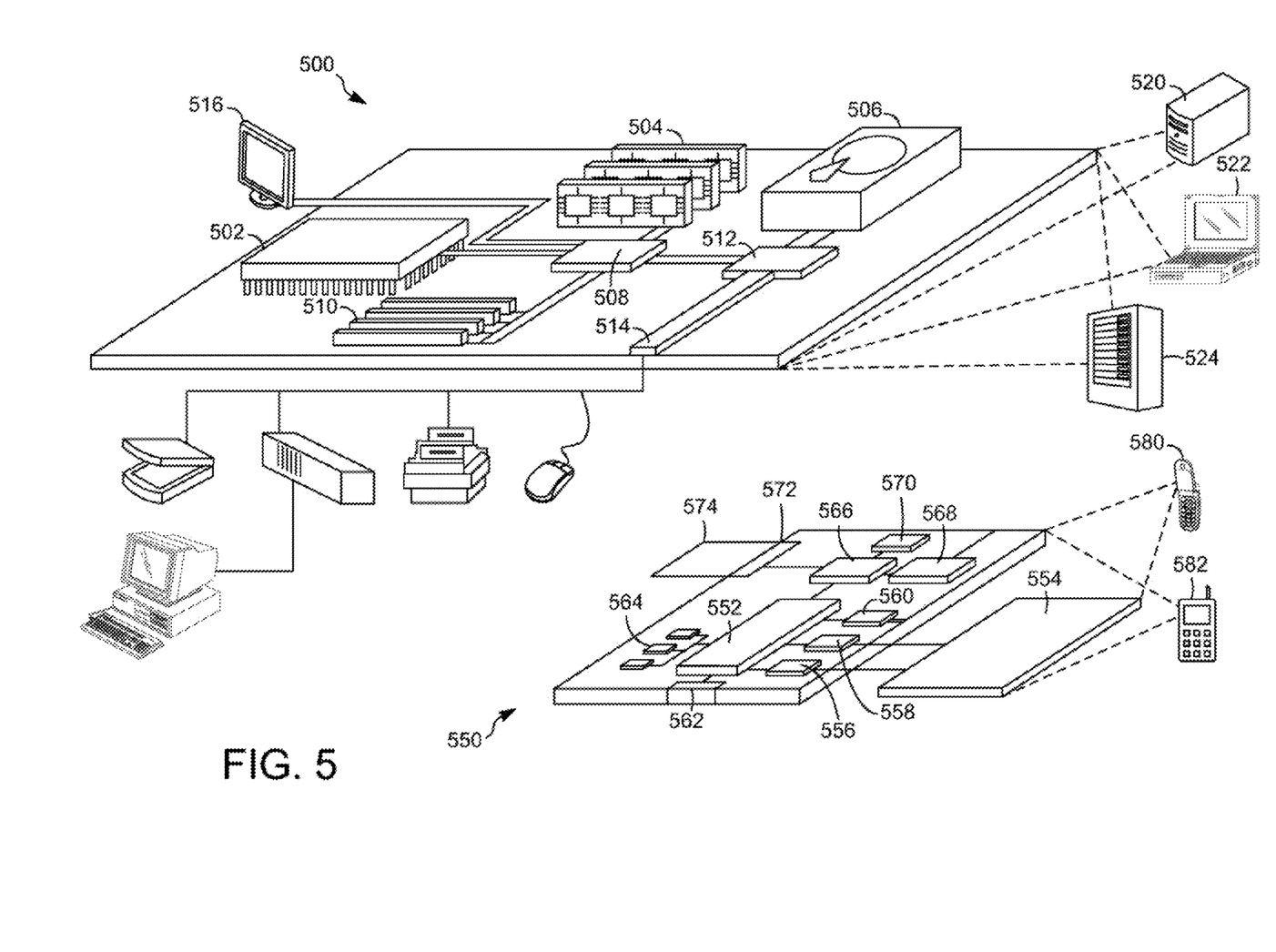
FIG. 5 is an exemplary computer system for processing reflected x-ray data.

FIG. 5 is a block diagram showing example or representative computing devices and associated elements that may be used to implement the systems method and apparatus described herein. FIG. 5 shows an example of a generic computing device 500 and a generic mobile computing device 550, which may be used with the techniques described here. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface or controller 508 connecting to memory 504 and high-speed expansion ports 510, and a low-speed interface or controller 512 connecting to low-speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504A or on the storage device 506 to display graphical information for a GUI on an external input/output device, such as display 516 coupled to high-speed controller 508A. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a volatile memory unit or units. In another implementation, the memory 504 is a non-volatile memory unit or units. The memory 504 may also be another form of computer-readable medium, such as a magnetic or optical disk.

The storage device 506 is capable of providing mass storage for the computing device 500. In one implementation, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low-speed controller 512 manages lower bandwidth-intensive operations. Such allocation of functions is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed bus 514. The low-speed bus 514, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 200A may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can execute instructions within the computing device 550, including instructions stored in the memory 564. The processor may be implemented as a chipset of chips that include separate and multiple analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554A may be, for example, a TFT LCD (Thin-Film-Transistor Liquid Crystal Display) or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication in some implementations, or for wireless communication in other implementations, and multiple interfaces may also be used.

The memory 564 stores information within the computing device 550. The memory 564 can be implemented as one or more of a computer-readable medium or media, a volatile memory unit or units, or a non-volatile memory unit or units. Expansion memory 574A may also be provided and connected to device 550A through expansion interface 572, which may include, for example, a SIMM (Single In Line Memory Module) card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provide as a security module for device 550, and may be programmed with instructions that permit secure use of device 550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552, that may be received, for example, over transceiver 568 or external interface 562.

Device 550 may communicate wirelessly through communication interface 566, which may include digital signal processing circuitry where necessary. Communication interface 566A may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, Wife, or other such transceiver (not shown). In addition, GPS (Global Positioning system) receiver module 570 may provide additional navigation- and location-related wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound (e.g., voice messages, music files, etc.) and may also include sound generated by applications operating on device 550.

The computing device 550 may be implemented in a number of different forms, as shown in the figure. For example, it may be implemented as a cellular telephone 580. It may also be implemented as part of a smart phone 582, personal digital assistant, a computer tablet, or other similar mobile device.

Thus, various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system (e.g., computing device 500 and/or 550) that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In the example embodiment, computing devices 500 and 550 are configured to receive and/or retrieve electronic documents from various other computing devices connected to computing devices 500 and 550 through a communication network, and store these electronic documents within at least one of memory 504, storage device 506, and memory 564. Computing devices 500 and 550 are further configured to manage and organize these electronic documents within at least one of memory 504, storage device 506, and memory 564 using the techniques described herein.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It will be appreciated that the above embodiments that have been described in particular detail are merely example or possible embodiments, and that there are many other combinations, additions, or alternatives that may be included. For example, while online gaming has been referred to throughout, other applications of the above embodiments include online or web-based applications or other cloud services.

Also, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "identifying" or "displaying" or "providing" or the like, refer to the action and processes of a computer system, or similar electronic computing device, that manipulates and transforms data represented as physical (electronic) quantities within the computer system memories or registers or other such information storage, transmission or display devices.

Based on the foregoing specification, the above-discussed embodiments of the invention may be implemented using computer programming or engineering techniques including computer software, firmware, hardware or any combination or subset thereof. Any such resulting program, having computer-readable and/or computer-executable instructions, may be embodied or provided within one or more computer-readable media, thereby making a computer program product, i.e., an article of manufacture, according to the discussed embodiments of the invention. The computer readable media may be, for instance, a fixed (hard) drive, diskette, optical disk, magnetic tape, semiconductor memory such as read-only memory (ROM) or flash memory, etc., or any transmitting/receiving medium such as the Internet or other communication network or link. The article of manufacture containing the computer code may be made and/or used by executing the instructions directly from one medium, by copying the code from one medium to another medium, or by transmitting the code over a network.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A method for imaging x-rays comprising:
   generating line x-ray radiation having a wavelength of or within plus or minus five percent of 0.9518 or 0.9454 angstroms resulting from an x-ray emitting event;
   receiving the line x-ray radiation at a crystal, the crystal comprising germanium;
   reflecting the line x-ray radiation from the crystal to a detector to form reflected line x-ray radiation; and
   receiving the reflected line x-ray radiation at the detector, the detector capable of capturing the reflected line x-ray radiation.

2. The method of claim 1, wherein the x-ray emitting event comprises a plasma.

3. The method of claim 2, wherein the plasma has a temperature of greater than 1 million degrees Celsius.

4. The method of claim 1, wherein the detector is an image plate.

5. The method of claim 1, wherein the germanium crystals has a Miller indices of one of the following indices: (9,7,3) or (11,3,3).

6. The method of claim 1, where a reflection angle formed between the line x-ray radiation and the reflected line x-ray radiation is within 10 degrees of normal.

7. The method of claim 1, wherein the line x-ray radiation is generated by alpha lines of helium-like krypton.

8. The method of claim 1, further comprising, prior to reflecting the x-ray radiation, bending the crystal to form an ellipsoidal or spherical shape.

9. The method of claim 1, wherein the detector comprises a CCD camera configured to generate a detector signal representing the x-ray radiation.

10. A crystal for x-ray reflection of x-ray radiation having a wavelength of 0.9518 or 0.9454 angstroms, the crystal comprising a crystal including germanium, with reflection planes defined by one or more of the following Miller indices: (9,7,3), (11,3,3).

11. The crystal of claim 10, wherein the reflection plane of the crystal is bent into a spherical or ellipsoidal shape.

12. The crystal of claim 10, wherein the crystal is configured to reflect radiation generated by alpha lines of helium-like krypton.

13. The crystal of claim 10, wherein a reflection from the reflection plane is within 10 degrees of normal.

14. A system for recording x-ray radiation comprising:
    a crystal aligned to receive radiation along a first path from an x-ray emitting event, the crystal having a reflection plane defined by one of the following Miller indices: (9,7,3) or (11,3,3);
    a detector aligned to receive reflected x-rays that are reflected from the crystal along a second path, the detector generating a detector signal in response to reflected x-rays impacting the detector;
    a processor configured to receive and process the detector signal to generate reflection data representing the x-rays emitted from the x-ray emitting event.

15. The system of claim 14, wherein the reflection data is presented on a display screen in 2 dimensional graphical format.

16. The system of claim 14, wherein the x-rays are x-rays generated by alpha lines of helium-like krypton.

17. The system of claim 14, wherein a reflection angle between the first path and the second path is 90 degree plus/minus 10 degrees.

18. The system of claim 14, wherein the crystal is formed from germanium.

19. The system of claim 14, wherein the reflection plane is formed into a spherical or ellipsoidal shape.

* * * * *